(12) United States Patent
Stengele (10) Patent No.: US 9,790,243 B2
(45) Date of Patent: *Oct. 17, 2017

(54) PHOTOCLEAVABLE LINKER MOLECULES WITH DIARYLSULPHIDE BACKBONE FOR TRANSIENT BIOCONJUGATE SYNTHESIS

(71) Applicant: Ventana Medical Systems, Inc., Tucson, AZ (US)

(72) Inventor: Klaus-Peter Stengele, Pleiskirchen (DE)

(73) Assignee: Ventana Medical Systems, Inc., Tucson, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/432,403

(22) PCT Filed: Sep. 27, 2013

(86) PCT No.: PCT/EP2013/070148
§ 371 (c)(1),
(2) Date: Mar. 30, 2015

(87) PCT Pub. No.: WO2014/053397
PCT Pub. Date: Apr. 10, 2014

(65) Prior Publication Data
US 2015/0284415 A1 Oct. 8, 2015

(30) Foreign Application Priority Data
Oct. 4, 2012 (EP) ................................. 12187286

(51) Int. Cl.
*C07F 9/24* (2006.01)
*C07F 9/6561* (2006.01)
*A61K 47/48* (2006.01)

(52) U.S. Cl.
CPC ...... *C07F 9/6561* (2013.01); *A61K 47/48092* (2013.01); *C07F 9/2429* (2013.01)

(58) Field of Classification Search
CPC ............................................... A61K 47/48092
See application file for complete search history.

(56) References Cited

U.S. PATENT DOCUMENTS 7,432,368 B2 * 10/2008 Stengele ............... C07H 19/04
536/18.5
2003/0171570 A1 9/2003 Schweitzer
(Continued)

FOREIGN PATENT DOCUMENTS

EP 1589024 A1 10/2005
JP 2004-500403 A 1/2004
(Continued)

OTHER PUBLICATIONS

Hasan, A. et al., "Photolabile Protecting Groups for Nucleosides: Synthesis and Photodeprotection Rates," Tetrahedron, vol. 53, No. 12, pp. 4247-4264 (1997).
Nielsen, P., et al., "Sequence-Selective Recognition of DNA by Strand Displacement with a Thymine-Substituted Polyamide," Science, vol. 254, pp. 1497-1500 (1991).
Olejnik, J. et al., "Photoclevable biotin derivatives: A versatile approach for the isolation of biomolecules," Proc. Natl. Acad. Sci. USA, vol. 92, pp. 7590-7594 (Aug. 1995).
Olejnik, J. et al., "Photoclevable aminotag phosphoramidites for 5'-termini DNA/RNA lableing," Nucleic Acids Research, vol. 26, No. 15, pp. 3572-3576 (1998).
(Continued)

*Primary Examiner* — Theodore R West
(74) *Attorney, Agent, or Firm* — Ventana Medical Systems, Inc.

(57) ABSTRACT

The present description refers to photocleavable compounds which can be used as a photocleavable linker in order to link two biomolecules, such as oligonucleotides and peptides. The present description further refers to a method for the synthesis of said photocleavable compounds.

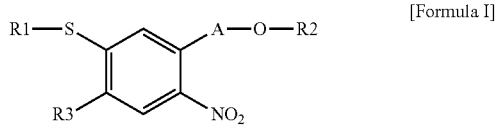

[Formula I]

9 Claims, 4 Drawing Sheets

Mol. Wt.: 907,06

(56) References Cited

U.S. PATENT DOCUMENTS

| | | |
|---|---|---|
| 2006/0079486 A1 | 4/2006 | Zalipsky |
| 2006/0167240 A1 | 7/2006 | Weiss et al. |
| 2008/0227968 A1 | 9/2008 | Komatsu et al. |
| 2011/0092693 A1 | 4/2011 | Natt et al. |

FOREIGN PATENT DOCUMENTS

| | | |
|---|---|---|
| JP | 2007-28993 A | 2/2007 |
| JP | 2008-516056 A | 5/2008 |
| JP | 2008-517950 A | 5/2008 |
| JP | 2009-523746 A | 6/2009 |
| WO | 2004074300 A2 | 9/2004 |

OTHER PUBLICATIONS

Olejnik, J. et al., "Photocleavable peptide-DNA conjugates: synthesis and applications to DNA analysis using MALDI-MS," Nucleic Acids Research, vol. 27, No. 23, pp. 4626-4631 (1999).

Pease, A., et al., "Light-generated oligonucleotide arrays for rapid DNA sequence analysis," Proc. Natl. Acad. Sci. USA, vol. 91, pp. 5022-5026 (May 1994).

Stengele K-P, et al., "Recent Highlights on Photolithic Oligonucleotide Array in Situ Synthesis," Nucleosides, Nucleotides and Nucleic Acids, 24: 5-7, pp. 891-896 (2005).

* cited by examiner

Fig. 1

Mol. Wt.: 907,06

PHOTOCLEAVABLE LINKER MOLECULES WITH DIARYLSULPHIDE BACKBONE FOR TRANSIENT BIOCONJUGATE SYNTHESIS

BACKGROUND OF THE INVENTION

The present description refers to photocleavable compounds which can be used as a photocleavable linker in order to link two biomolecules, such as oligonucleotides and peptides. The present description further refers to a method for the synthesis of said photocleavable compounds.

Photocleavable compounds play an important role as protecting groups in blocking functional groups present in nucleosides, nucleotides, sugars and amino acids, which are used for the synthesis of biomolecules, e.g. nucleic acids and their derivatives, proteins, peptides and carbohydrates. Such compounds have the advantage that deprotection of the protected functional group can be performed simply via light exposure. Therefore, photocleavable compounds provide the basis for the photolithography based spatially resolved synthesis of oligonucleotides or peptides on solid supports, such as microarrays. The use of photolabile compounds for the synthesis of microarrays is well known (Pease, et al. Proc. Natl. Acad. Sci. USA 91 (1994) 5022-5026), Hasan, et al. Tetrahedron 53 (1997) 4247-4264).

Photocleavable compounds can also be used as photocleavable linker molecules to link different elements, such as two biomolecules, a biomolecule and a solid phase, a biomolecule and streptavidin. For example, two different oligonucleotides may be connected via the photocleavable compound in order to deliver a single stranded molecule to a biochemical or biological assay, which upon irradiation with light releases the two individual oligonucleotides which then may form a double stranded DNA and exhibit biological function. Another possible application is that an oligonucleotide may be linked to a biotin molecule via a photocleavable compound such that the oligonucleotide may be captured by affinity purification, e.g. by streptavidin coated magnetic beads from an assay and secondly may be released from the affinity resin by irradiation with light.

Yet another possible application is that the aforementioned oligonucleotide-photocleavable-compound-biotin structure may be useful in pull-down purifications or assays, when the oligonucleotide is a protein binding aptamer.

The elements, which are photocleavably connected by the above mentioned compounds can be separated from each other simply due to light exposure. Such components are well known (Olejnik, et al. Proc. Natl. Acad. Sci. USA 92 (1995) 7590-7594; Olejnik, et al. Nucleic Acids Res. 26 (1998) 3572-3576; Olejnik, et al. Nucleic Acids Res. 27 (1999) 4626-4631).

The major drawback of photocleavable compounds described in the art is that light in the near UV-range (365 nm or shorter) has to be used for cleaving the covalent bond(s) in order to cleave the photocleavable compound. Light sources, which are suitable to generate such wavelength, are e.g. mercury arc lamps, excimer lasers, UV-LEDs and frequency multiplied solid-state lasers. Such light sources are characterized by high purchase costs, provide limited luminous power and have a short life-time leading to high overall costs of operation. Since some of the above mentioned light sources contain hazardous substances, e.g. mercury, appropriate actions to secure occupational safety and proper disposal are necessary further increasing the costs.

Some of the above mentioned light sources produce a broad spectrum of wavelengths, e.g. mercury arc lamps emit light from the UV- to the IR-range, both of which have disadvantageous effects if used in the context of biomolecules. UV-light for example can be absorbed by the synthesized DNA leading to random breaks within the strand by phosphate backbone radical cleavage, guanine base oxidation and subsequent strand break or photodimerization, especially of thymine bases. Furthermore, UV-light can also lead to the destruction of certain amino acids, such as tryptophan by radical oxidation or cysteine and methionine by sulfur oxidation. As a result, experiments involving biomolecules are influenced by the use of such UV-light for the cleavage of the photocleavable compounds. In contrast, IR-light leads to warming of the experimental setup which also influences the results of the experiments.

The object of the present description is therefore the provision of photocleavable compounds, which do not show the above mentioned drawbacks.

BRIEF DESCRIPTION OF THE INVENTION

The present description refers to a photocleavable compound which can be used as a photocleavable linker in order to link two biomolecules, such as oligonucleotides and peptides. Upon radiation with visible light, the linker is cleaved, thereby releasing the two biomolecules. More precisely, the present description refers to a photocleavable compound of the formula

[Formula I]

wherein A is —$CH_2$—, —$CH_2$—$CH_2$—, —$CH(CH_3)$—, —$CH(CH_3)$—$CH_2$—, and R3 is H, a methyl group or an ethyl group, and R2 is a phosphoramidite, H-phosphonate, phosphate diester or phosphate triester, wherein, when R2 is a phosphate diester of the formula —O—P(O)—(OR4)-(OH), R4 is alkyl or substituted alkyl or a nucleoside or an oligonucleotide, and wherein, when R2 is a phosphate triester of the formula —O—P(O)—(OR4)-(OR5), R4 and R5 each is alkyl or substituted alkyl or a nucleoside or an oligonucleotide or together form an internucleotide moiety of an oligonucleotide, and R1 is a phenylcarboxylic amide, wherein a functional group is bound via the amino group to the phenylcarboxylic amide.

The present description further relates to a method for preparing a photocleavable compound as described above comprising the steps of a) provision of p-diethylbenzene as a starting material, b) bromination of the phenylring, c) nitration of the obtained compound in Nitric- and Sulfuric Acid in the position para- to the Bromine, d) purification and crystallization, e) hydroxymethylation of the compound at the benzylic position, f) conversion of the aromatic bromine group to the arylsulfide using substituted thiophenol, g) purification, h) conversion of the alcohol to chlorocarbonate, i) reaction of the chlorocarbonate with a nucleoside and reaction of the nucleoside with a phosphitylating agent, or reaction of the chlorocarbonate with an amino acid derivative.

DETAILED DESCRIPTION OF THE INVENTION

The following definitions are set forth to illustrate and define the meaning and scope of various terms used herein.

The letter A in the group -A-O— represents a "fragmentation linker" comprising from 1 to 2 linearly, covalently connected atoms such as methylene- or ethylene-. The term "fragmentation linker" is used herein as known to the expert skilled in the art and relates to a moiety which is used as a moiety in photochemistry that effects the light-induced fission of the photocleavable compound by transforming the primary photoprocess into a chemical cleavage reaction.

The term "alkyl" denotes a monovalent linear or branched saturated hydrocarbon group of 1 to 12 carbon atoms. In particular embodiments, alkyl has 1 to 7 carbon atoms, and in more particular embodiments 1 to 4 carbon atoms. Examples of alkyl include methyl, ethyl, propyl, isopropyl, n-butyl, iso-butyl, sec-butyl, or tert-butyl.

The term "amino" denotes a group of the formula —NR'R" wherein R' and R" are independently hydrogen, alkyl, alkoxy, cycloalkyl, heterocycloalkyl, aryl or heteroaryl. Alternatively, R' and R", together with the nitrogen to which they are attached, can form a heterocycloalkyl. The term "primary amino" denotes a group wherein both R' and R" are hydrogen. The term "secondary amino" denotes a group wherein R' is hydrogen and R" is not. The term "tertiary amino" denotes a group wherein both R' and R" are not hydrogen. Particular secondary and tertiary amines are methylamine, ethylamine, propylamine, isopropylamine, phenylamine, benzylamine dimethylamine, diethylamine, dipropylamine and diisopropylamine.

The term "aryl" denotes a monovalent aromatic carbocyclic mono- or bicyclic ring system comprising 6 to 10 carbon ring atoms. Examples of aryl moieties include phenyl and naphthyl.

The term "biomolecule" is used herein as known to the expert skilled in the art and refers to any organic molecule that is produced by a living organism or to any artificially produced derivatives of such compounds, including large polymeric molecules such as proteins, polysaccharides, carbohydrates, lipids, nucleic acids and oligonucleotides as well as small molecules such as primary metabolites, secondary metabolites, and natural products.

The term "functional group" is used herein as known to the expert skilled in the art and refers to any of numerous combinations of atoms that form parts of chemical molecules, that undergo characteristic reactions themselves, and that in many cases influence the reactivity of the remainder of the molecule. Typical functional groups are hydroxyl, carboxyl, aldehyde, carbonyl, amino, azide, alkynyl, thiol and nitril.

The term "heteroaryl" denotes a monovalent aromatic heterocyclic mono- or bicyclic ring system of 5 to 12 ring atoms, comprising 1, 2, 3 or 4 heteroatoms selected from N, O and S, the remaining ring atoms being carbon. Examples of heteroaryl moieties include pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, azepinyl, diazepinyl, isoxazolyl, benzofuranyl, isothiazolyl, benzothienyl, indolyl, isoindolyl, isobenzofuranyl, benzimidazolyl, benzoxazolyl, benzoisoxazolyl, benzothiazolyl, benzoisothiazolyl, benzooxadiazolyl, benzothiadiazolyl, benzotriazolyl, purinyl, quinolinyl, isoquinolinyl, quinazolinyl, or quinoxalinyl.

The term "internucleotide moiety" is used herein as known to the expert skilled in the art and refers to any covalently attached atoms or molecules, which form a bridge between two nucleosides. A typical internucleotide moiety in DNA is a phosphodiester moiety.

The terms "nucleic acid" or "polynucleotide" can be used interchangeably and refer to a polymer that can be corresponded to a ribose nucleic acid (RNA) or deoxyribose nucleic acid (DNA) polymer, or an analog thereof. This includes polymers of nucleotides such as RNA and DNA, as well as synthetic forms, modified (e.g., chemically or biochemically modified) forms thereof, and mixed polymers (e.g., including both RNA and DNA subunits). Exemplary modifications include methylation, substitution of one or more of the naturally occurring nucleotides with an analog, internucleotide modifications such as uncharged linkages (e.g., methyl phosphonates, phosphotriesters, phosphoamidates, carbamates, and the like), pendent moieties (e.g., polypeptides), intercalators (e.g., acridine, psoralen, and the like), chelators, alkylators, and modified linkages (e.g., alpha anomeric nucleic acids and the like). Also included are synthetic molecules that mimic polynucleotides in their ability to bind to a designated sequence via hydrogen bonding and other chemical interactions. Typically, the nucleotide monomers are linked via phosphodiester bonds, although synthetic forms of nucleic acids can comprise other linkages (e.g., peptide nucleic acids as described in Nielsen, et al., Science 254 (1991) 1497-1500). A nucleic acid can be or can include, e.g., a chromosome or chromosomal segment, a vector (e.g., an expression vector), an expression cassette, a naked DNA or RNA polymer, the product of a polymerase chain reaction (PCR), an oligonucleotide, a probe, and a primer. A nucleic acid can be, e.g., single-stranded, double-stranded, or triple-stranded and is not limited to any particular length. Unless otherwise indicated, a particular nucleic acid sequence comprises or encodes complementary sequences, in addition to any sequence explicitly indicated.

The term "nucleoside" is used herein as known to the expert skilled in the art and refers to molecules with a nitrogen containing base moiety, such as purine or pyrimidine, wherein the base moiety is linked to a pentose, such as deoxyribose, ribose, arabinose, xylose or lyxose, or wherein the base moiety is linked to a hexose sugar moiety. Typical purine or pyrimidine bases which form nucleosides include adenine, guanine, cytosine, thymine, 5-methyl cytosine and uracil.

The term "oligonucleotide" generally refers to a nucleic acid sequence typically designed to be single-stranded DNA and less than 75 nucleotides in length.

The term "peptide" is used herein as known to the expert skilled in the art and refers to organic compounds made of amino acids arranged in a linear chain and joined together by peptide bonds between the carboxyl and amino groups of adjacent amino acid residues.

The term "phosphoramidite" is used herein as known to the expert skilled in the art and refers to a nucleoside linked via a sugar hydroxyl moiety to a (III)-valent phosphor, which itself is linked via oxygen to a protective group, like beta-cyanoethoxy- and to a dialkylated nitrogen.

The term "photocleavable" is used herein as known to the expert skilled in the art and refers to a group having specific bonds which can be cleaved by irradiation at specific wavelengths. The term "photocleavable compound" refers to a compound that contains a moiety dissociating into two or more independent molecules upon irradiation, in particular irradiation with light.

The term "protecting group" denotes the group which selectively blocks a reactive site in a multifunctional compound such that a chemical reaction can be carried out selectively at another unprotected reactive site in the meaning conventionally associated with it in synthetic chemistry. Protecting groups can be removed at the appropriate point. Exemplary protecting groups are amino-protecting groups, carboxy-protecting groups or hydroxy-protecting groups.

Photo labile protecting groups of the state-of-the-art according to the description, include, but are not limited to, 2-Nitrobenzyloxycarbonyl-(NBOC), 2-nitrophenyl-ethyl-oxycarbonyl (NPEOC), 2-(3,4-methylenedioxy-2-nitrophenyl)-propyloxycarbonyl (MeNPPOC), 2-(3,4-methylenedioxy-2-nitrophenyl)-oxycarbonyl (MeNPOC), 2-(2-nitrophenyl)-propyloxycarbonyl (NPPOC), dimethoxybenzo-inylyl-oxycarbonyl (DMBOC), 2-(2-nitrophenyl)-ethylsulfonyl (NPES), (2-nitrophenyl)-propylsulfonyl (NPPS), and the like.

The term "saturated" in context with the definition of the term linking group is used herein as known to the expert skilled in the art and relates to a linking group in which all members of the group are connected to the respective adjacent atom(s) through single bonds. Accordingly, a saturated hydrocarbon chain is represented by the formula —$(CH_2)_n$— with n being an integer ranging from 1 to 2.

The term "solid support" is used herein as known to the expert skilled in the art and refers to any insoluble and rigid or semi-rigid inorganic or organic material, having a large surface area to which surface organic molecules can be attached through bond formation or absorbed through electronic or static interactions such as through bond formation through a functional group.

The term "substituted" denotes that a specified group bears one or more substituents. Where any group can carry multiple substituents and a variety of possible substituents is provided, the substituents are independently selected and need not to be the same. The term "unsubstituted" means that the specified group bears no substituents. The term "optionally substituted" means that the specified group is unsubstituted or substituted by one or more substituents, independently chosen from the group of possible substituents. When indicating the number of substituents, the term "one or more" means from one substituent to the highest possible number of substitution, i.e. replacement of one hydrogen up to replacement of all hydrogens by substituents.

The present description relates to photocleavable compounds of the formula

[Formula I]

wherein A is —$CH_2$—, —$CH_2$—$CH_2$—, —$CH(CH_3)$—, —$CH(CH_3)$—$CH_2$—, and R3 is H, a methyl group or an ethyl group, and R2 is a phosphoramidite, H-phosphonate or phosphate diester or phosphate triester, wherein, when R2 is a phosphate diester of the formula —O—P(O)—(OR4)-(OH), R4 is alkyl or substituted alkyl or a nucleoside or an oligonucleotide, and wherein, when R2 is a phosphate triester of the formula —O—P(O)—(OR4)-(OR5), R4 and R5 each is alkyl or substituted alkyl or a nucleoside or an oligonucleotide or together form an internucleotide moiety of an oligonucleotide, and R1 is a phenylcarboxylic amide, wherein a functional group is bound via the amino group to the phenylcarboxylic amide.

In one embodiment the functional group is selected from the group consisting of 4,4'-dimethoxytrityl-oxy-alkyl-, trifluoroacetyl-amino-alkyl-, alkylamido-biotin and hapten.

In one embodiment A is —$CH(CH_3)$—$CH_2$—. In one embodiment R3 is an ethyl group. In one embodiment R2 is a phosphoramidite.

In another embodiment a first molecule is bound to the functional group and a second molecule is bound to the phosphoramidite. The first molecule can be bound to the functional group via an amino-alkyl-group or an oxy-alkyl-group. The second molecule can be bound to the phosphoramidite by standard oligonucleotide synthesis.

In yet another embodiment, the first molecule and the second molecule can be any biomolecule. In one embodiment the first and the second molecule is independently selected from the group consisting of proteins, peptides, polysaccharides, carbohydrates, lipids, nucleic acids, oligonucleotides, primary metabolites, secondary metabolites, and natural products. In a specific embodiment, the first and the second molecule is independently selected from the group consisting of peptides and oligonucleotides. In another embodiment, the first molecule is DNA and the second molecule is DNA. In another embodiment, the first molecule is a peptide and the second molecule is DNA, or vice versa.

The photocleavable compound according to the description can be cleaved by using visible light in a range from 375 nm to 420 nm. In a specific embodiment, visible light is used in the range from 390 to 405 nm. In a more specific embodiment, visible light is used at 390 nm or 405 nm, respectively. Both wavelengths can be generated using light sources which are much less expensive as compared to light sources necessary to perform deprotection in the near UV range at approximately 365 nm. In one embodiment solid state lasers within the range from 375 nm to 420 nm, especially at 390 nm and 405 nm, are used as light sources to perform the cleaving reaction according to the description. In a more specific embodiment, LEDs (light emitting diodes) with sufficient emission within the range from 375 nm to 420 nm, especially at 390 nm and 405 nm, are used as light sources to perform the cleaving reaction according to the description. Especially LEDs are low cost products as they are produced in high quantities, e.g. for the use in Blu-ray Players.

Within the cleaving reaction of the photocleavable compound according to the description stabilizing agents known by the skilled person can be present, which increase the effectiveness of the cleaving reaction and suppressing side reactions of the light-generated radicals. As stabilizing agents one may use a combination of a base and a reducing compound, such as Imidazole, Hydroxylamine, Benzalacetone and similar.

In a specific embodiment, the functional group is selected from the group consisting of 4,4'-dimethoxytrityl-oxy-alkyl-, trifluroacetyl-amino-alkyl- and alkylamido-biotin, A is —$CH(CH_3)$—$CH_2$—, R3 is an ethyl group, R2 is a phosphoramidite, a first molecule is bound to the functional group and a second molecule is bound to the phosphoramidite, wherein the first and the second molecule is independently selected from the group consisting of peptides and oligonucleotides and wherein the cleaving reaction can be performed at a wavelength from 375 nm to 420 nm.

Figure 1:
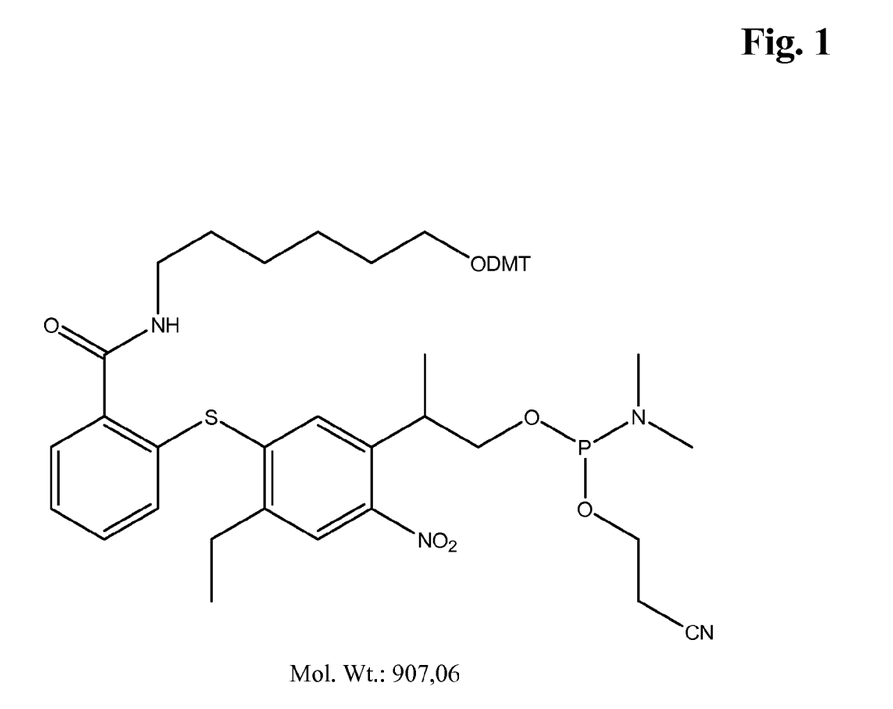
FIG. 1: The figure shows a photocleavable spacer amidite as a building block for oligonucleotide synthesis.
Figure 4:
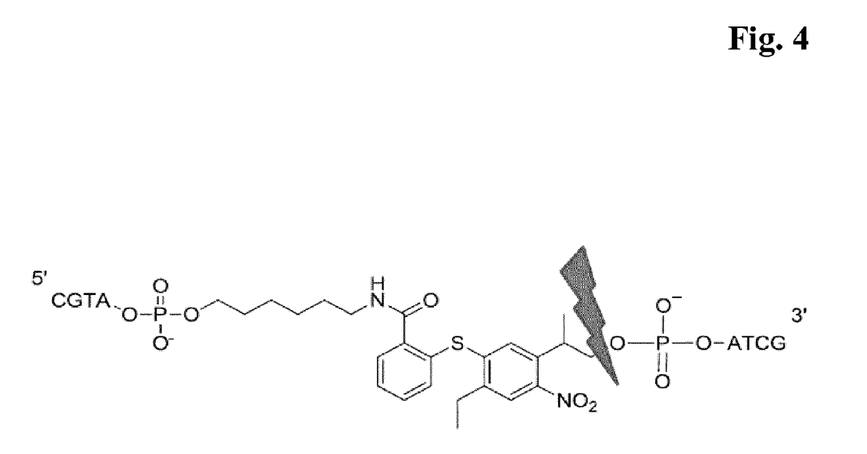
FIG. 4: The figure shows two exemplary oligonucleotides linked by a photocleavable linker and indication of the cleavage site upon irradiation by light.

In one embodiment, a photocleavable spacer amidite as depicted in FIG. 1 may be used to extend an oligonucleotide at its 5'-end during chemical oligonucleotide synthesis. Subsequently, the DMT group is removed by standard methods in oligonucleotide synthesis and a second oligonucleotide may be synthesized on the free OH-group, rendering at the end of the synthesis an oligonucleotide as shown in FIG. 4, wherein the photocleavable compound is present and may be cleaved by light at the position indicated by arrow.

Figure 2:
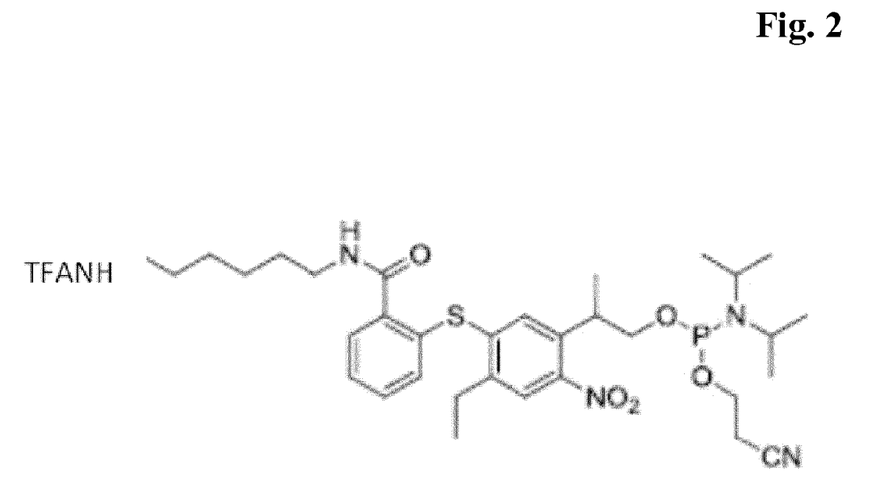
FIG. 2: The figure shows a photocleavable amino-modifier amidite as a building block for oligonucleotide synthesis.

In one embodiment, the compound as shown in FIG. 2 will release an oligonucleotide with a 5'-free-amino group, that may be coupled e.g. to a peptide or an antibody in order to perform an assay known as "Immuno-PCR", which can later be photolytically cleaved into the oligonucleotide and the antibody, e.g. for array based multiplexing analysis. Furthermore, DNA directed immobilization of antibodies or proteins may be accomplished in a photo-reversible manner.

Figure 3:
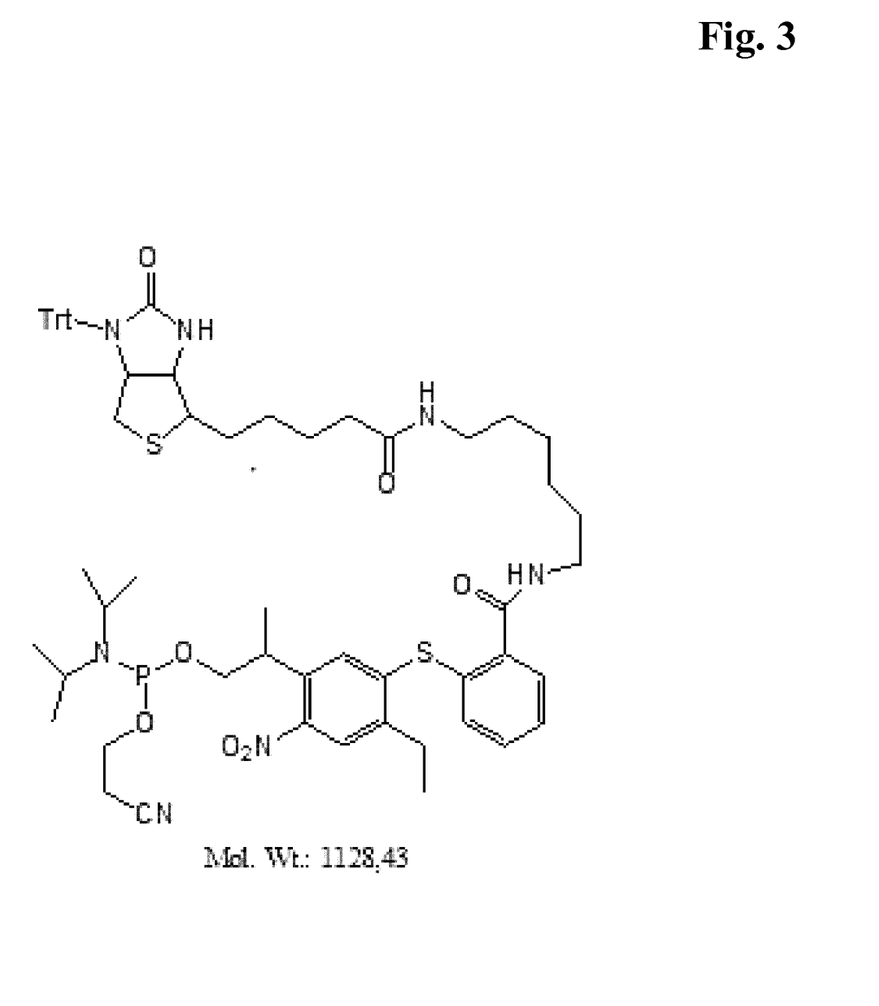
FIG. 3: The figure shows a photocleavable biotin-modifier amidite as a building block for oligonucleotide synthesis.

In one embodiment, the compound as shown in FIG. 3 may be used for methods in which aptamer like oligonucleotides carrying a biotin molecule via a photocleavable linker are used to purify the appropriate target protein from a complex biological sample as a sample enrichment strategy, when the captured aptamer-protein complexes are cleaved by light from the affinity matrix.

The present description further refers to a method for preparing a photocleavable compound as described above comprising the steps of a) provision of p-diethylbenzene as a starting material, b) bromination of the phenylring, c) nitration of the obtained compound in Nitric- and Sulfuric Acid in the position para- to the Bromine, d) purification and crystallization, e) hydroxymethylation of the compound at the benzylic position, f) conversion of the aromatic bromine group to the arylsulfide using substituted thiophenol, g) purification, h) conversion of the alcohol to chlorocarbonate, i) reaction of the chlorocarbonate with a nucleoside and reaction of the nucleoside with a phosphitylating agent, or reaction of the chlorocarbonate with an amino acid derivative.

In one embodiment A is —CH(CH$_3$)—CH$_2$—. In One embodiment R3 is an ethyl group. In one embodiment R2 is a phosphoramidite.

In one embodiment the functional group is selected from the group consisting of 4,4'-dimethoxytrityl-oxy-alkyl-, trifluroacetyl-amino-alkyl-, alkylamido-biotin and hapten.

The following examples are provided to aid the understanding of the present description, the true scope of which is set forth in the appended claims. It is understood that modifications can be made in the procedures set forth without departing from the spirit of the description.

Example 1

Synthesis of a Photocleavable Spacer Amidite as a Building Block for Oligonucleotide Synthesis 231 g of 2,5-diethyl-4-nitrobenzene (0.895 mol), 106.2 g thiosalicylic acid (0.688 mol) and 285 g potassium carbonate (2.064 mol) are heated to reflux in 1.2 L dimethylformaide (DMF) for 1 h. DMF is then distilled in vacuo, the residue diluted with water to a total volume of 3.5 L and extracted 6 times with 0.5 L with hexaneethyl acetate 1:1. The aqueous residue is adjusted to pH 6.0 with dilute HCl and extracted twice with 0.5 L ethyl acetate, which are combined and washed with 1 L water. Ethyl acetate is removed by a Rotavap, the residue is dissolved in dichloromethane and purified by column chromatography on silica dichloromethane.

Yield: 173.1 g (76%) Amorphous Reddish Foam after Evaporation (P3-Acid).

173 g of P3-acid (0.522 mol), 59 g paraformaldehyde (0.652 mol) and 437 g triton B (40% in MeOH=1.044 mol) are heated to 90° C. in 1.4 L DMSO for 2 h. After cooling, 0.2 L acetic acid and 6 L water are added. It is extracted with 1 L dichloromethane, washed twice with 0.2 L water and evaporated in vacuo. The solid residue crystallizes upon standing, is triturated in little dichloromethane and filtered with suction.

$^1$H-NMR (300 MHz, DMSO):

13.32 ppm (s, 1H, COOH); 7.95 ppm (dd, 1H, Ar—H thiosalicyl); 7.83 ppm (s, 1H, Ar—H nitroaromat); 7.56 ppm (s, 1H, Ar—H nitroaromat); 7.46-7.38 ppm (m, 1H, Ar—H thiosalicyl); 7.32-7.25 ppm (m, 1H, Ar—H thiosalicyl); 6.73 ppm (d, 1H, Ar—H thiosalicyl); 4.75 ppm (s, 1H, OH); 3.44 ppm (d, 2H, Ar—C(CH$_3$)H—CH$_2$—OH); 3.26-3.11 ppm (m, 1H, Ar—C(CH$_3$)H—CH$_2$—OH); 2.68 ppm (q, 2H, CH$_2$ of Ar-Et); 1.19-1.08 ppm (m, 6H, 2×CH$_3$)

Yield: 82 g (43%) Yellowish Crystals (P3-Acid-Alcohol)

16.0 g P3-acid-alcohol (44.3 mmol), 16.0 g t-BdMS-Cl (106 mmol) and 14.5 g N-methylimidazole (177 mol) are stirred at room temperature (RT) in 0.1 L dichloromethane overnight. The mixture is extracted 3 times with each 0.4 L water and evaporated. The solid residue is dissolved in 0.2 L methanol, 16 g potassium carbonate are added and stirred for 90 min at 40° C. About 70% of methanol is removed in vacuo, 0.2 L water are added, acidified with citric acid to about pH 2.0 and extracted with ethyl acetate. The extracts are washed with water and evaporated to a clear brownish oil (22.7 g; 108%, P3-acid-(tBdMS-ether) which is used in the next step without further purification and characterization.

4.9 g P3-acid-(tBdMS-ether) are dissolved in 30 mL dichloromethane and charged with 2.2 g N-ethyl-N'-diethylaminopropyl-carbodiimid*HCl and stirred for 45 min at RT. A solution of 4.9 g O-dimethoxytrityl-1-amino-6-hexanol in 15 mL dichloromethane is added and stirring is continued over night. The mixture is washed with water, the organic residue extracted twice with sat. NaCl/water and evaporated in vacuo.

The residue is purified by column chromatography (silica, dichloromethane-methanol gradient) and evaporated to yield a yellow foam.

4.4 g (50%) of tBdMS-Protected Photocleavable-Spacer $^1$H-NMR (300 MHz, DMSO):

8.39 ppm (t, 1H, amid-H); 7.72 ppm (s, 1H, Ar—H nitroaromat); 7.55-7.47 ppm (m, 1H, Ar—H); 7.40-7.32 ppm (m, 4H, Ar—H); 7.30-7.16 (m, 9H, Ar—H); 7.08-7.02 ppm (m, 1H, Ar—H); 6.90-6.82 ppm (m, 4H, Ar—H); 3.72 ppm (s, 6H, 2× methoxy of DMT); 3.59-3.46 ppm (m, 2H, Ar—C(CH$_3$)H—CH$_2$-OTBDMS); 3.33-3.24 ppm (m, 1H, Ar—C(CH$_3$)H—CH$_2$-OTBDMS); 3.25-3.14 ppm (m, 2H, R—CH$_2$—O-DMT); 2.97-2.91 ppm (m, 2H, R—CH$_2$—NH—CO—R'); 2.67 ppm (q, 2H, CH$_2$ of Ar-Et); 1.56-1.20 ppm (m, 8H, 4×CH$_2$ "Mittelteil Hexyl"); 1.12-1.04 ppm (m, 6H, CH$_3$ of Ar-Et+Ar—C(CH$_3$)H—CH$_2$-OTBDMS); 0.71 ppm (s, 9H, t-Bu of TBDMS); 0.14 ppm (d, 6H, Si(CH$_3$)$_2$ of TBDMS).

Removal of the tBdMS-group is accomplished by stirring in a mixture of 3 g TBAF*3*H$_2$O in 30 mL THF for 1 h at RT.

The mixture was washed with sodium bicarbonate solution, evaporated in vacuo and purified by column chromatography (silica, dichloromethane-methanol gradient 2%) and evaporated to yield a yellow foam.

Yield: 2.9 g (76%) Photocleavable Spacer Alcohol $^1$H-NMR (300 MHz, DMSO):

8.33 ppm (t, 1H, amid-H); 7.71 ppm (s, 1H, Ar—H nitroaromat); 7.53-7.46 ppm (m, 1H, Ar—H); 7.44-7.33 ppm (m, 4H, Ar—H); 7.33-7.11 (m, 10H, Ar—H); 6.92-6.84 ppm (m, 4H, Ar—H); 4.74 ppm (t, 1H, R—OH); 3.73 ppm (s, 6H, 2× methoxy of DMT); 3.35-3.31 ppm (m, 2H, Ar—C(CH$_3$)H—CH$_2$—OH); 3.25-3.11 ppm (m, 3H, R—CH$_2$—O-DMT+Ar—C(CH$_3$)H—CH$_2$—OH); 2.98-2.90 ppm (m, 2H, R—CH$_2$—NH—CO—R'); 2.67 ppm (q, 2H, CH$_2$ of Ar-Et); 1.56-1.18 ppm (m, 8H, 4×CH$_2$ centerbody hexyl); 1.13 ppm (t, 3H, CH$_3$ of Ar-Et); 1.03 ppm (d, 3H, Ar—C(CH$_3$)H—CH$_2$—OH)

2.9 g photocleavable spacer alcohol are dissolved in 30 mL dry dichloromethane and charged with 0.68 g cyanoethyl-tetraisopropyl-phosphorodiamidite and 0.22 g dicyanoimidazole and stirred overnight under argon.

The reaction mixture was diluted with hexanes until slight turbidity remains and purified by column chromatography (silica, hexanes-ethylacetate gradient 4:1-1:1) and evaporated to yield a yellow foam.

Yield: 0.95 g (25%) Photocleavable Spacer Amidite of FIG. 1

HPLC: 92.4% pure $^1$H-NMR (300 MHz, DMSO):

8.38 ppm (m, 1H, amid-H); 7.74 ppm (s, 1H, Ar—H nitroaromat); 7.54-7.46 ppm (m, 1H, Ar—H); 7.40-7.16 ppm (m, 12H, Ar—H); 7.12-7.00 ppm (m, 1H, Ar—H); 6.92-6.82 ppm (m, 4H, Ar—H); 3.72 ppm (s, 6H, 2× methoxy of DMT); 3.68-3.34 ppm (m, 7H, Ar—C(CH$_3$)H—CH$_2$—OPA+Ar—C(CH$_3$)H—CH$_2$—OH+2×CH$_2$ of cyanoethyl); 3.24-3.14 ppm (m, 2H, R—CH$_2$—O-DMT); 2.97-2.90 ppm (m, 2H, R—CH$_2$—NH—CO—R'); 2.73-2.61 ppm (m, 4H, CH$_2$ of Ar-Et+2×CH of iso-propyl); 1.57-1.39 ppm (m, 4H, 2×CH$_2$ centerbody hexyl); 1.39-1.21 ppm (m, 4H, 2×CH$_2$ centerbody hexyl); 1.21-0.90 ppm (m, 18H, 6×CH$_3$).

$^{31}$P-NMR (121.53 MHz, DMSO):

143.76 ppm; 143.24 ppm.

Example 2

Synthesis of the Compound of FIG. 2: Photocleavable Amino-Modifier-Amidite

In a similar manner, the photocleavable amino-modifier was prepared from P3-acid-(tBdMS-ether) and N-triflouroacetyl-1,6-diaminohexane to yield the title compound in 12% overall yield (4 steps).

Example 3

Synthesis of the Compound of FIG. 3: Photocleavable Biotin-Modifier-Amidite

In a similar manner, the photocleavable biotin-modifier was prepared from P3-acid-(tBdMS-ether) and N-dimethoxytrityl-biotin-6-aminocaproylamide to yield the title compound in 9% overall yield (4 steps).

The invention claimed is:

1. A photocleavable compound of formula I

[Formula I]

wherein A is —CH$_2$—, —CH$_2$—CH$_2$—, —CH(CH$_3$)— or —CH(CH$_3$)—CH$_2$—,

R3 is H, a methyl group or an ethyl group,

R2 is a phosphoramidite, H-phosphonate, phosphate diester or phosphate triester, wherein, when R2 is a phosphate diester of the formula —O—P(O)-(OR4)-(OH), R4 is an alkyl or substituted alkyl or a nucleoside or an oligonucleotide, and wherein, when R2 is a phosphate triester of the formula —O—P(O)-(OR4)-(OR5), R4 and R5 each is alkyl or substituted alkyl or a nucleoside or an oligonucleotide or together form an internucleotide moiety of an oligonucleotide, R1 is a phenylcarboxylic amide, and wherein a functional group is bound via the amino group to the phenylcarboxylic amide.

2. The compound according to claim 1, wherein the functional group is selected from the group consisting of 4,4'-dimethoxytrityl-oxy-alkyl-, trifluroacetyl-amino-alkyl-, alkylamido-biotin and a hapten.

3. The compound according to claim 1 wherein A is —CH(CH$_3$)—CH$_2$—.

4. The compound according to claim 1 wherein R3 is an ethyl group.

5. The compound according to claim 1 wherein R2 is a phosphoramidite.

6. The compound according to claim 1 further comprising a first molecule bound to the functional group and a second molecule bound to the phosphoramidite.

7. The compound according to claim 6, wherein the first molecule and the second molecule is are independently selected from the group consisting of oligonucleotide and peptide.

8. The compound according to claim 1 wherein said photocleavable compound is cleaved at a wavelength from 375 nm to 420 nm.

9. A method for preparing the photocleavable compound according to claim 1 comprising the steps of
  a) Provision of p-diethylbenzene as a starting material
  b) Bromination of the phenyl ring
  c) Nitration of the obtained compound in nitric- and sulfuric acid in the position para- to the bromine
  d) Purification and crystallization
  e) Hydroxymethylation of the compound at the benzylic position
  f) Conversion of the aromatic bromine group to the arylsulfide using substituted thiophenol
  g) Purification
  h) Conversion of the alcohol to chlorocarbonate
  i) Reaction of the chlorocarbonate with a nucleoside and reaction of the nucleoside with a phosphitylating agent, or
  Reaction of the chlorocarbonate with an amino acid derivative,
thereby obtaining a compound of Formula I.

* * * * *